United States Patent [19]

Kawata et al.

[11] 4,055,721
[45] Oct. 25, 1977

[54] METHOD OF PRODUCING UNSATURATED CARBONYL COMPOUNDS

[75] Inventors: Noboru Kawata; Kosaku Honna; Hirozo Sugahara, all of Sodegaura, Japan

[73] Assignee: Idemitsu Kosan Company, Ltd., Tokyo, Japan

[21] Appl. No.: 702,987

[22] Filed: July 6, 1976

[30] Foreign Application Priority Data
July 10, 1975    Japan .................................. 50-84010

[51] Int. Cl.² ........................................... C07C 69/54
[52] U.S. Cl. .................................. 560/207; 560/104; 260/533 AN
[58] Field of Search ................. 260/486 AC, 533 AN

[56] References Cited
U.S. PATENT DOCUMENTS
3,904,672   9/1975   Knifton ..................... 260/486 AC FOREIGN PATENT DOCUMENTS
1,138,760   10/1962   Germany ..................... 260/486 AC OTHER PUBLICATIONS
Tsuji; J. et al., J. Org. Chem., 31, 2641–2643 (1966).

Primary Examiner—Paul J. Killos
Attorney, Agent, or Firm—Flynn & Frishauf

[57] ABSTRACT

Unsaturated carbonyl compounds such as methyl methacrylate are produced by reacting an acetylene, CO and water or an alcohol in the presence of a catalyst comprising a Pd(II) compound and a compound R″X where R″ is H, lower alkyl or aryl and X is halogen, and in the presence of an oxygen-containing compound other than water or an alcohol.

10 Claims, No Drawings

METHOD OF PRODUCING UNSATURATED CARBONYL COMPOUNDS

FIELD OF THE INVENTION

This invention relates to a method of producing unsaturated carbonyl compounds. More particularly, it relates to an efficient method of producing unsaturated carbonyl compounds in the presence of specified catalysts and specified oxygen-containing compounds.

BACKGROUND OF THE INVENTION

Heretofore, methods of producing unsaturated carbonyl compounds using acetylene compounds as starting materials have been widely known. For instance, a method using a Pd compound containing a small amount of an organic phosphine as a catalyst, and a method of utilizing a soluble salt of a metal belonging to Group VIII of the periodic table with an organic compound of phosphorus, arsenic, antimony or bismuth are known. However, these methods have disadvantages in that reaction must be carried out at a relatively high temperature and yield of desired product may decrease due to catalyst employed.

Recently, another method using palladium black and an alkyl halide or a hydrogen halide as a catalyst has been developed. However, this method also has disadvantages in that inactivation of catalyst occurs rapidly, inpurities such as allene act as inhibitors for the reaction, and satisfactory selectivity cannot be obtained.

SUMMARY OF THE INVENTION

We have tried to overcome disadvantages of the conventional methods, and have found that when Pd(II) compounds and halides are used as the catalyst, remarkable improvement in selectivity can be attained and catalyst activity can be maintained highly for long periods of time, when and oxygen-containing compound is included.

In accordance with the present invention, there is provided a method of producing unsaturated carbonyl compounds of the formula $CH_2=CR-COOR'$ wherein R is hydrogen, lower alkyl or aryl group and $R'$ is hydrogen or lower alkyl group, by reaction of a compound of the formula $RC\equiv CR$ (wherein each R is the same as designated above), carbon monoxide and a compound of the formula $R'OH$ (wherein $R'$ is the same as designated above), in the presence of a catalyst comprising a Pd(II) compound and a compound of the formula $R''X$ wherein $R''$ is hydrogen, a lower alkyl or an aryl group and X is halogen, and in the presence of an oxygen-containing compound other than a compound of the formula $R'OH$.

The reaction involved in the present invention can be indicated as follows:

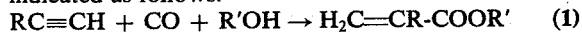

Acetylene compounds of the formula $RC\equiv CH$ which are used as reactants in this method include by way of illustration: acetylene, methyl acetylene, ethyl acetylene and phenyl acetylene. An acetylene containing an impurity such as allene or propylene can also be used; purity of the starting material is not required for practicing this invention.

Examples of compounds of the formula $R'OH$ are water and lower alcohols such as mehtanol, ethanol and propanol.

The catalysts comprise a Pd(II) compound and a specified halogenated compound of the formula $R''X$. Examples of PD(II) compounds used in the present invention are PD(II)-halide, Pd(II)-acetate, PD(II)-nitrate and PD(II)-sulfate. The halogenated component of the catalyst is a hydrogen halide, lower alkyl halide or aryl halide. Typical examples of such compounds are: hydrogen iodide, hydrogen bromide, hydrogen chloride, hydrogen fluoride, methyl iodide, methyl bromide, methyl chloride, methyl fluoride, ethyl iodide, ethyl bromide, ethyl chloride, ethyl fluoride and phenyl iodide. Iodide compounds such as hydrogen iodide, methyl iodide and ethyl iodide are preferred examples.

As to molar ratios of the components of the catalysts, the ratio of PD(II) compound to halogenated compound is from about 1/20 to about 1/1, preferably approximately 1/10–1/1. When the molar ratio is below about 1/20, selectivity of methyl methacrylate is lowered. A Pd(II) compound is used in an amount of from about 0.1 to about 5.0%. (mole), preferably 0.1 to 1.0% (mole), based on the amount of acetylene compouund. When the amount of Pd(II) compound is less than about 0.01% (mole), selectivity of methyl methacrylate is decreased extensively and the object of the present invention cannot be obtained.

The reaction indicated by formula (1), above, has been carried out previously in a solvent represented by the formula $R'OH$, and thus decrease of catalyst activity is drastic and sufficient selectivity is not obtained. In order to overcome these disadvantages, a specified oxygen-containing compound is used as a solvent for the reaction in the present invention, in place of $R'OH$. In the present invention, $R'OH$ is used in an amount approximating the amount of the acetylene compound ($RC\equiv CR$). However, it is necessary to use a relatively large amount, preferably from about 2 to about 10 times, of the oxygen-containing compound as a solvent, based upon the amount (volume) of the $R'OH$ compound employed. Examples of the oxygen-containing compounds are esters of carboxylic acids, ethers and ketones. Typical examples are methyl acetate, ethyl acetate, methyl benzoate, tetrahydrofuran, diethyl ether, dioxane, acetone, methyl ethyl ketone, acetyl acetone, etc.

Oxygen-containing compounds having an unsaturated bond other than an unsaturated aromatic compound are not preferred in the process of this invention, since these compounds cause a decrease in selectivity of the desired product.

Also, compounds of the formula $R'OH$ are excluded from the oxygen-containing compounds contemplated herein, since unsatisfactory results are obtained, as illustrated below, when a desired oxygen-containing compound is omitted.

The method of the present invention is carried out under pressure in a pressure-resisting containing in which an acetylene compound, carbon monoxide, water or lower alcohol ($R'OH$), catalyst and an oxygen-containing compound are placed. The reaction temperature is from room temperature (about 20° C.) to about 120° C., preferably 50°–100° C. Reaction time is from about 1 to about 3 hours, preferably about 2 hours. The reaction pressure is from about 20 to about 40 kg/cm² as a partial pressure for carbon monoxide, when the reaction temperature is about room temperature. When the pressure is lower, decrease in selectivity is observed.

According to the method of the present invention, catalyst activity can be maintained for a relatively longer period of time than with palladium black catalyst. Formation of unsaturated carboxylic acids or their esters such as acrylic acid or its ester from acetylene, metharcrylic acid or its ester from methyl acetylene, α-phenyl acrylic acid or its ester from phenyl acetylene, etc., can be achieved by only one step under mild conditions with high conversion yield and high selectivity. Furthermore, amounts of strong corrosive halides can be reduced to approximately 1/10 based on amounts used in conventional methods. Further, allene does not act as a reaction inhibitor in the method of this invention.

Moreover, the starting material, acetylene, can be supplied easily from a cracked gas which is a by-product from cracking of petroleum distillates. The method has advantages of utilizing starting material of relatively low coat and utilizing cracked gas effectively. Furthermore, methyl methacrylate which is widely used for the production of transparent plastics can be produced at substantially lower cost than in conventional methods.

This invention is illustrated by the following examples.

EXAMPLE 1

Into a 100 ml. autoclave made of a titanium alloy were charged 75 millimoles (3 g) of methyl acetylene, 15 ml of methyl acetate, and prescribed amounts of methanol, Pd(II) compound and hydrogen iodide (57 weight percent of aqueous solution). The resulting mixture was stirred and was heated therein to 50° C., and carbon monoxide was charged therein to provide a pressure of 24 kg/cm². After 1.5 hours, the autoclave was cooled down rapidly by water and then carbon monoxide was released. The reaction product was confirmed by gas chromatography as being the desired compound. Actual conditions of the reaction and results are shown in Table 1. Experiments without an oxygen-containing compound, i.e., methyl acetate, and with palladium black as a catalyst, were also made and the results thereof are shown in Table 1. As is obvious from these results, improvement of conversion yield and reduction in amounts of halogen compounds can be achieved when one of the oxygen-containing compounds is used.

Table 2

| Ethyl Acetate (ml) | Ethanol (ml) | Conversion yield of Methyl Acetylene (%) | Methyl Methacrylate (millimole) | Ethyl Crotonate (millimole) | Selectivity of Methyl Methacrylate (%) |
|---|---|---|---|---|---|
| 0 | 30 | 75.0 | 2.95 | trace | 5.2 |
| 20 | 8 | 94.1 | 42.4 | 1.93 | 60.0 |

EXAMPLE 3

Into a 100 ml autoclave made of a titanium alloy were charged, 75 millimoles (3 g) of methyl acetylene, about 180 millimoles of various oxygen-containing compounds, 123 millimoles (5 ml) of methanol, 0.25 millimole of PD(II) chloride and 1.0 millimole of hydrogen iodide. The resulting mixture was stirred and was heated to 50° C. and then carbon monoxide was introduced to provide a pressure of 24 kg/cm². After 1.5 hours, the autoclave was cooled down rapidly by water and then carbon monoxide was released. The reaction product was analyzed by gas chromatography and confirmed to be the material desired. Conditions and results are shown in Table 3.

As is obvious from these results, improvement of selectivity of the material desired is achieved by using an oxygen-containing compound.

Table 3

| Oxygen-containing compound (ml) | Conversion Yield of Methyl Acetylene (%) | Methyl Methacrylate (millimole) | Methyl Crotonate (millimole) | Selectivity of Methyl Methacrylate (%) |
|---|---|---|---|---|
| Methyl acetate 15 | 92.2 | 38.7 | 1.59 | 56.0 |
| Methyl benzoate 23 | 86.8 | 41.1 | 2.4 | 63.1 |
| Tetrahydrofuran 15 | 74.0 | 31.0 | 1.53 | 56.0 |
| Toluene 20 | 75.7 | 30.7 | — | 54.0 |
| Acetyl acetone 20 | 73.0 | 35.0 | 1.86 | 63.9 |
| Acetone 15 | 84.0 | 48.5 | 2.62 | 77.2 |
| Methyl ethyl ketone 20 | 93.5 | 53.0 | 4.33 | 75.6 |
| Acetone 15 | 94.4* | 39.7 | 0.93 | 93.4 |
| Acetone 15 | 97.0** | 36.5 | 0.91 | 94.2 |

*Amounts of methyl acetylene is 45 millimole (1.8 g).
**Amounts of methyl acetylene is 40 millimole (1.6 g).

Table 1

| PdCL₂ (millimole) | HI (millimole) | Methyl Acetate (ml) | Methanol (ml) | Conversion Yield of Methyl Acetylene (%) | Methyl Methacrylate (millimole) | Methyl Crotonate (millimole) | Selectivity of Methyl Methacrylate (%) |
|---|---|---|---|---|---|---|---|
| 0.5 | 10 | 15 | 5 | 92.1 | 26.3 | 1.57 | 38.0 |
| 0.25 | 1 | 15 | 5 | 92.2 | 38.7 | 1.59 | 56.0 |
| 0.5 | 10 | 0 | 20 | 79.5 | 25.6 | 2.10 | 43.0 |
| 0.25 | 1 | 0 | 20 | 37.2 | 1.91 | 0.21 | 6.8 |
| 0.25* | 1 | 15 | 5 | 51.0 | 15.8 | 1.80 | 41.2 |

*Pd-black was used instead of PdCl₂

EXAMPLE 2

Experiments similar to those described in Example 1 were carried out, except that 75 millimoles (3 g) of methyl acetylene, prescribed amounts of ethyl acetate, prescribed amounts of ethanol, 0.25 millimole of PD(II) chloride and 1 millimole of hydrogen iodide (57 weight percent of aqueous solution) were placed in a 100 ml autoclave made of a titanium alloy. Results are shown in Table 2.

EXAMPLE 4

The same experiment as described in Example 3 was carried out, except that 75 millimoles (3 g) of methyl acetylene, 15 ml of acetone, 123 millimoles (5 ml) of methanol, 0.25 millimole of Pd(II) chloride and prescribed amounts of hydrogen halides were placed in a 100 ml autoclave made of titanium alloy. The reaction was conducted for 2 hours. Results are shown in Table 4.

From these results, it is obvious that excellent catalyst activity and good selectivity is realized with hydrogen bromide.

Table 4

| Hydrogen halide (millimole) | Conversion Yield of Methyl Acetylene (%) | Methyl Methacrylate (millimole) | Methyl Crotonate (millimole) | Selectivity of Methyl Methacrylate (%) |
|---|---|---|---|---|
| HBr 1.0 | 42.5 | 3.7 | 0.58 | 11.6 |
| HBr 5.0 | 84.0 | 41.3 | 2.5 | 66.0 |
| HCl 5.0 | 35.5 | 0.54 | trace | 2.0 |

EXAMPLE 5

The same experiment as described in Example 1 was carried out, except that prescribed amounts of mixtures of methyl acetylene and allene, 15 ml of oxygen-containing compound, 123 millimoles (5 ml) of methanol, 0.25 millimole of Pd(II) chloride and 1.0 millimole of Pd(II) chloride and 1.0 millimole of hydrogen iodide were placed in a 100 ml autoclave made of titanium alloy. Reaction was conducted for 100 minutes. Results are shown in Table 5.

From these results, it is obvious that selectivity of the desired compound is almost zero in the absence of an oxygen-containing compound, while in accordance with the method of the present invention, remarkable improvement in selectivity is attained.

Table 5

| Methyl Acetylene (millimole) | Allene (millimole) | Oxygen-containing Compound (ml) | Conversion Yield of Starting Material (%) | Methyl Methacrylate (millimole) | Methyl Crotonate (millimole) | Selectivity of Methyl Methacrylate (%) |
|---|---|---|---|---|---|---|
| 56 | 19 | methyl acetate 15 | 55.3 | 1.6 | trace | 3.8 |
| 65.6 | 9.4 | " | 56.0 | 7.7 | 0.23 | 18.3 |
| 56 | 19 | acetone 15 | 59.5 | 8.3 | 0.6 | 18.6 |
| 65.6 | 9.4 | " | 60.2 | 21.2 | 0.52 | 47.5 |
| 56 | 19 | —* | 50.0 | trace | trace | — |

*20 ml of methanol was used as reactant and solvent.

EXAMPLE 6

The same experiment as described in Example 3 was carried out, except that 75 millimoles (3 g) of methyl acetylene, 15 ml of acetone, 123 millimoles (5 ml) of methanol, 0.25 millimole of various Pd(II) compounds and 1.0 millimole of hydrogen iodide were placed in a 100 ml autoclave made of titanium alloy. Results are shown in Table 6.

Table 6

| Pd compound | Conversion Yield of Methyl Acetylene (%) | Methyl Methacrylate (millimole) | Selectivity of Methyl Methacrylate (%) | Methyl Crotonate (millimole) | Selectivity of Methyl Crotonate (%) |
|---|---|---|---|---|---|
| PdCl$_2$ | 84.0 | 48.5 | 77.0 | 2.62 | 4.2 |
| Pd(CH$_3$COO)$_2$ | 76.9 | 46.2 | 80.1 | 1.20 | 2.1 |
| Pd(NO$_3$)$_2$ | 86.4 | 51.2 | 79.0 | 1.20 | 1.9 |
| PdSO$_4$ | 78.9 | 46.1 | 77.9 | 1.00 | 1.7 |
| Pd-black* | 51.0 | 15.8 | 41.2 | 1.80 | 4.7 |

*Methyl acetate (15 ml) was used instead of acetone as the oxygen-containing compound.

EXAMPLE 7

The same experiment as described in Example 3 was made, except that 15 ml of methyl crotonate was used as an oxygen-containing compound. As a result, conversion yield of methyl methacrylate was 85.2%, amount of methyl methacrylate was 30.6 millimoles and selectivity was 47.8%.

EXAMPLE 8

Into a 100 ml autoclave made of titanium alloy were charged 45 millimoles (1.8%) of methyl acetylene, about 180 millimoles of acetone, 123 millimoles (5 ml) of methanol, 0.25 millimole of Pd(II) chloride and 1.0 millimole of hydrogen iodide. The resulting mixture therein was stirred and was heated to 50° C., and then carbon monoxide was introduced to provide a pressure of 24 kg/cm$^2$. After 1.5 hours, the autoclave was cooled down rapidly by water and then the resulting reaction product and carbon monoxide were removed; Only Pd(II) chloride remained in the autoclave. To the autoclave methyl acetylene, acetone, methanol and hydrogen iodide were added in the same amounts and the reaction was carried out again. The same experiment was so repeated 8 times and the life of the catalyst was examined. Results are shown in Table 7.

Table 7

| Reaction time | Conversion Yield of Methyl Acetylene (%) | Methyl Methacrylate (millimole) | Methyl Crotonate (millimole) | Selectivity of Methyl Methacrylate (%) |
|---|---|---|---|---|
| 1 | 92.2 | 40.1 | 1.08 | 96.6 |
| 2 | 55.1 | 21.5 | 0.96 | 86.7 |
| 3 | 53.5 | 22.5 | 0.87 | 93.3 |
| 4* | 74.6 | 31.9 | 1.05 | 94.9 |
| 5 | 67.1 | 28.9 | 1.00 | 95.0 |
| 6 | 70.0 | 27.0 | 1.30 | 85.7 |
| 7 | 71.3 | 26.9 | 0.66 | 83.7 |
| 8 | 52.8 | 20.8 | 0.45 | 87.4 |
| 9 | 82.2 | 35.4 | 1.07 | 95.6 |
| 10** | 90.4 | 36.7 | 0.86 | 90.2 |
| Average | 70.9 | 29.2 | 0.93 | 91.3 |

*Amounts of hydrogen iodide is 1.5 millimoles.
**Amounts of hydrogen iodide is 2.0 millimoles.

What is claimed is:
1. A method of producing an unsaturated carbonyl compound of the formula

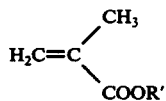

wherein R' is hydrogen or lower alkyl, which comprises reacting methyl acetylene, carbon monoxide and a compound of the formula R'OH wherein R' is hydrogen or lower alkyl in the presence of a catalyst consisting essentially of a palladium (II) compound and a compound of the formula R"X wherein R" is hydrogen, lower alkyl or aryl and X is iodine or bromine, and in the presence of an ester of a saturated aliphatic acid or a saturated aliphatic ketone, the amount of said R'OH compound being substantially equal to the amount of methyl acetylene and the amount of said ester or ketone being from about 2 to about 10 times the amount of said R'OH compound.

2. The method according to claim 1, wherein the ester or ketone is one selected from the group consisting of methyl acetate, ethyl acetate, methyl benzoate, acetone, methyl ethyl ketone and acetyl acetone.

3. The method according to claim 1, wherein the palladium(II) compound is one selected from the group consisting of Pd(II)-halide, Pd(II)-acetate, Pd(II)-nitrate and Pd(II)-sulfate.

4. The method according to claim 1, wherein the compound of the formula R'X is one selected from the group consisting of hydrogen iodide, hydrogen bromide, methyl iodide, methyl bromide, ethyl iodide, ethyl bromide and benzene iodide.

5. The method according to claim 1, wherein the molar ratio of the Pd(II) compound to the compound of the formula R"X is from about 1/20 to about 1/1.

6. The method according to claim 1, wherein the Pd(II) compound is used in an amount of from about 0.01 to about 5.0% (mole).

7. The method according to claim 1, wherein the reaction temperature is from about 20° C. to about 120° C.

8. The method according to claim 1, wherein the reaction time is from about 1 to about 3 hours.

9. The method according to claim 1, wherein the pressure is from about 20 to about 40 kg/cm$^2$ calculated as the partial pressure of the carbon monoxide.

10. The method according to claim 1, wherein the oxygen-containing compound is a saturated ester of a caboxylic acid.

* * * * *

UNITED STATES PATENT AND TRADEMARK OFFICE
CERTIFICATE OF CORRECTION

PATENT NO. : 4,055,721
DATED : October 25, 1977
INVENTOR(S) : NOBORU KAWATA et al It is certified that error appears in the above-identified patent and that said Letters Patent are hereby corrected as shown below:

Column 1, line 39: replace "and" with ---an---.

Column 2, lines 3, 4, 5 and 15; Column 3, line 64; and Column 4, line 15:

replace "PD(II)" with ---Pd(II)---.

Column 3, line 17: replace "coat" with ---cost---.

Column 3, Table 1, first column, heading: replace "PdCL$_2$" with ---PdCl$_2$---.

Signed and Sealed this

Fourth Day of July 1978

[SEAL]

Attest:

RUTH C. MASON
*Attesting Officer*

DONALD W. BANNER
*Commissioner of Patents and Trademarks*